United States Patent
Packard et al.

[11] Patent Number: 6,073,486
[45] Date of Patent: Jun. 13, 2000

[54] PIEZOELECTRIC GLIDE HEAD

[75] Inventors: Edward L. Packard, San Marcos; Jean-Marc Gery, Beverly Hills, both of Calif.

[73] Assignee: MicroGlide Inc., Colorado Springs, Colo.

[21] Appl. No.: 09/134,450

[22] Filed: Aug. 14, 1998

[51] Int. Cl.$^7$ ............................. G01B 5/28; G01N 19/08
[52] U.S. Cl. .................................................. 73/105
[58] Field of Search ................................................ 73/105

[56] References Cited

U.S. PATENT DOCUMENTS

| | | |
|---|---|---|
| 4,532,802 | 8/1985 | Yeack-Scranton et al. . |
| 5,423,207 | 6/1995 | Flechsig et al. . |
| 5,450,747 | 9/1995 | Flechsig et al. . |
| 5,689,064 | 11/1997 | Kennedy et al. ................... 73/105 |
| 5,864,054 | 1/1999 | Smith, Jr. ........................... 73/105 |

OTHER PUBLICATIONS

IBM Technical Disclosure Bulletin vol. 34 No. 4A, Sept. 1991, Efficient Piezoelectric Glide Transducer for Magnetic Recording Disk Quality Assurance.

IEEE Transactions on Magnetics, vol. 25, No. 3, Sept. 1989, Natural Frequencies of Sliders and Transducers Used to Detect Slider–Disk Contacts, T. G. Jeong et al., pp. 3725–3727.

IEEE Transactions on Magnetics, vol. 24, No. 6, Nov. 1988, Reproduction of Slider Vibrations During Head/Disk Interactions Using PZT Sensors, A. Wallash, pp. 2763–2765.

*Primary Examiner*—Daniel S. Larkin
*Attorney, Agent, or Firm*—Robert S. Kelly

[57] ABSTRACT

A glide head for detecting anomalies on a flat surface of a recording disk includes a slider having a sensing edge extending generally radially of the disk and a piezoelectric transducer element attached to one face of the slider and extending therefrom in cantilever fashion. The transducer element is of segmented shape and has a pair of opposed surfaces facing towards and away from the disk surface with spaced electrodes being provided thereon so as to provide stress readings only at specific locations on the body of the transducer element chosen to accentuate particular vibrational modes induced by anomalies on the disk surface.

26 Claims, 5 Drawing Sheets

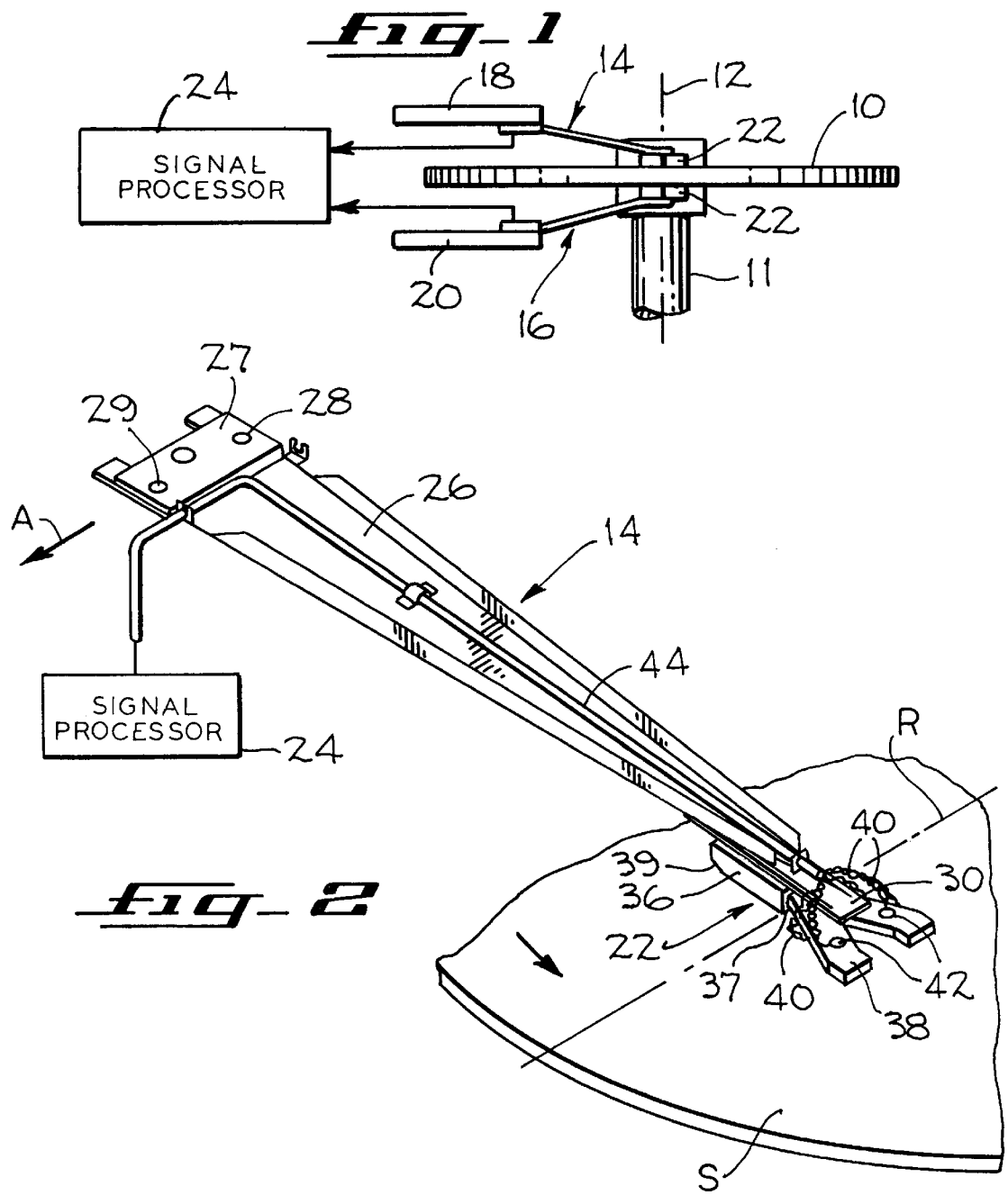

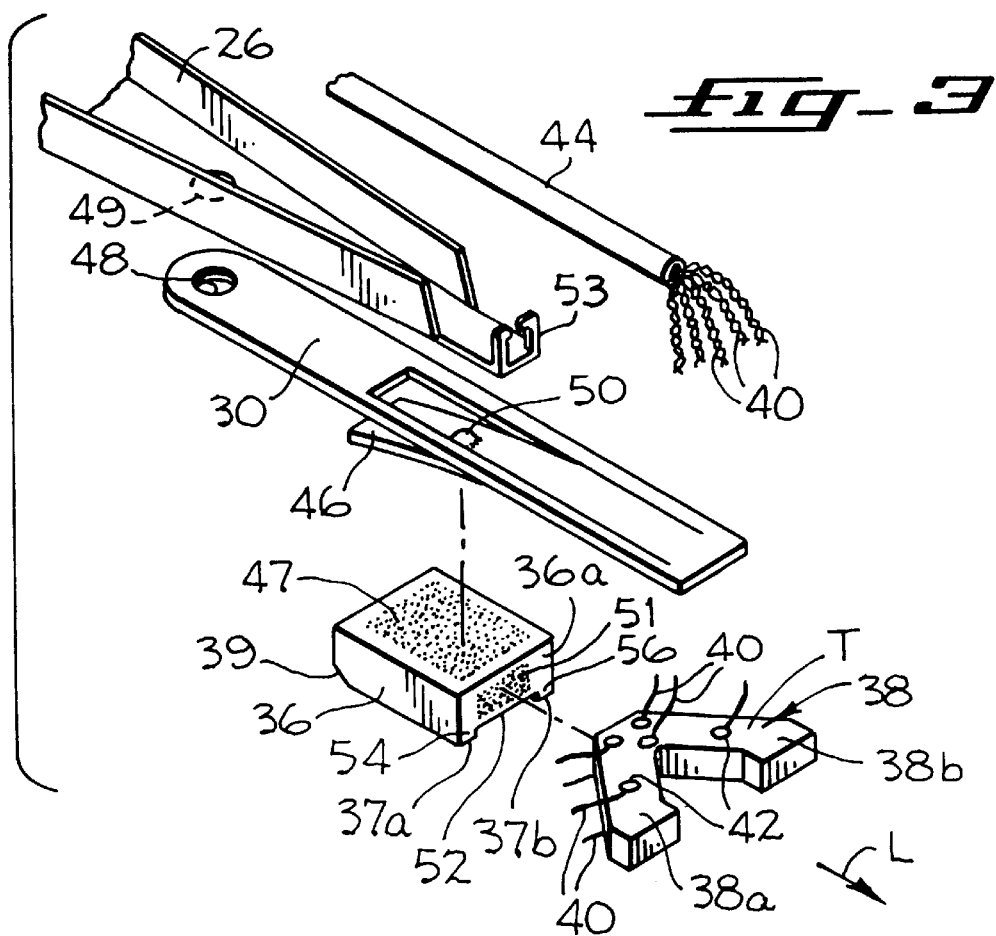
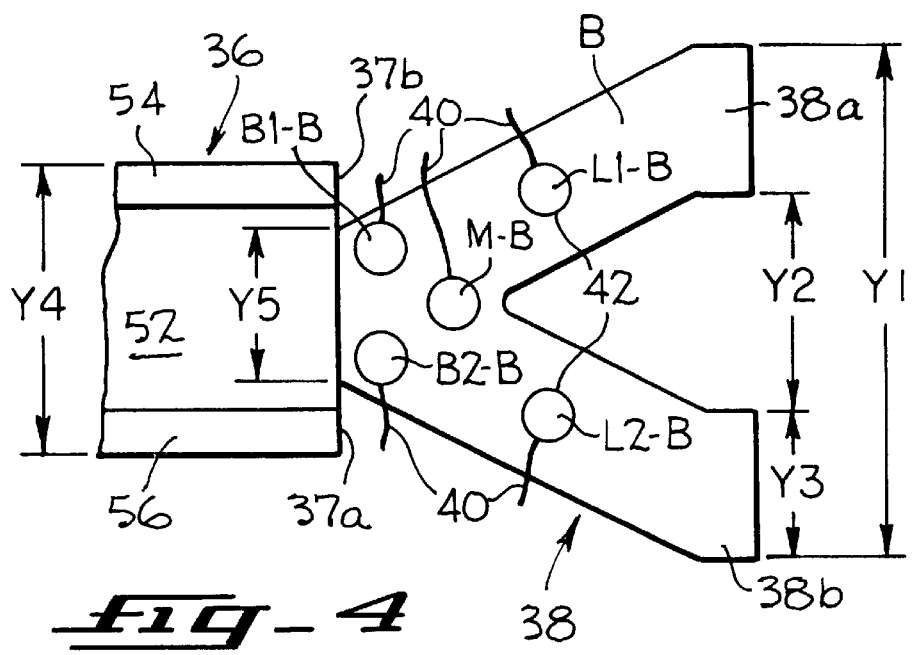

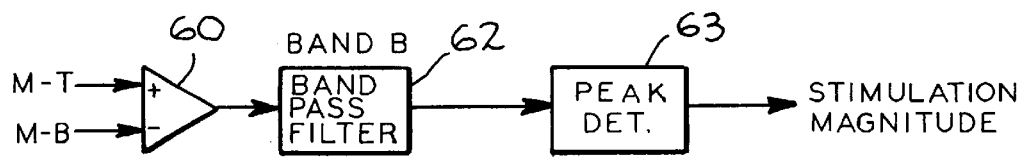
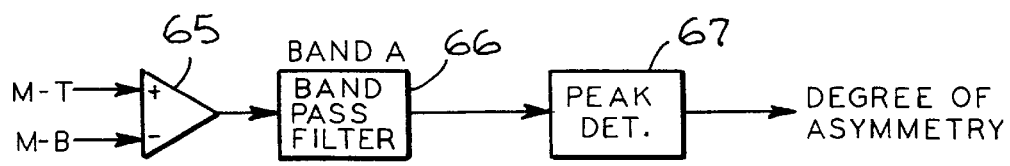
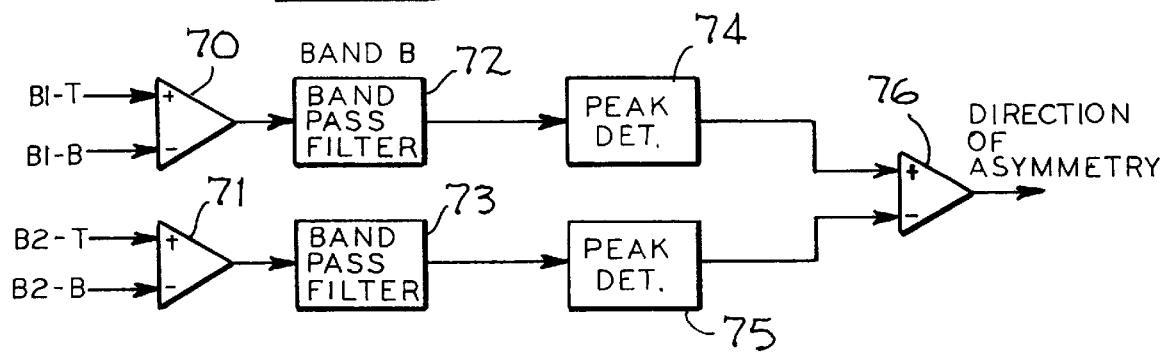
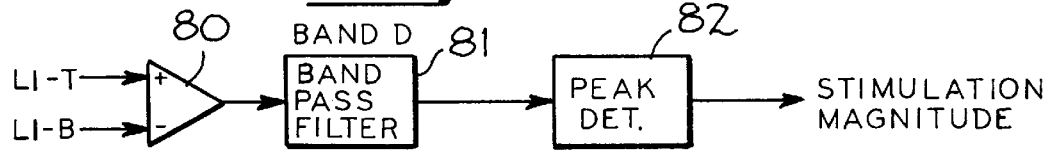
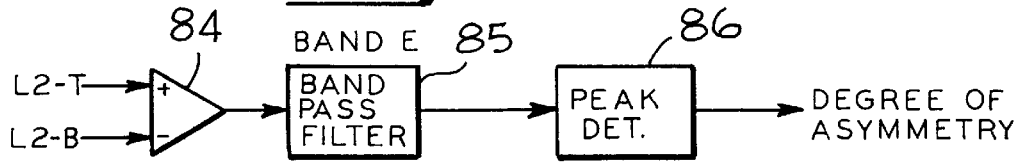

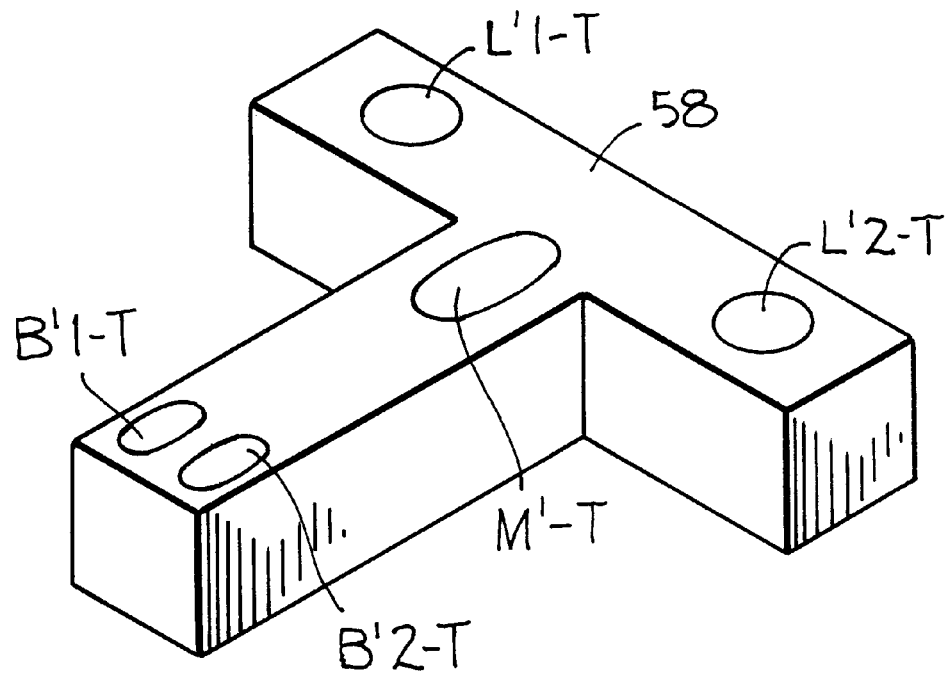
fig_6
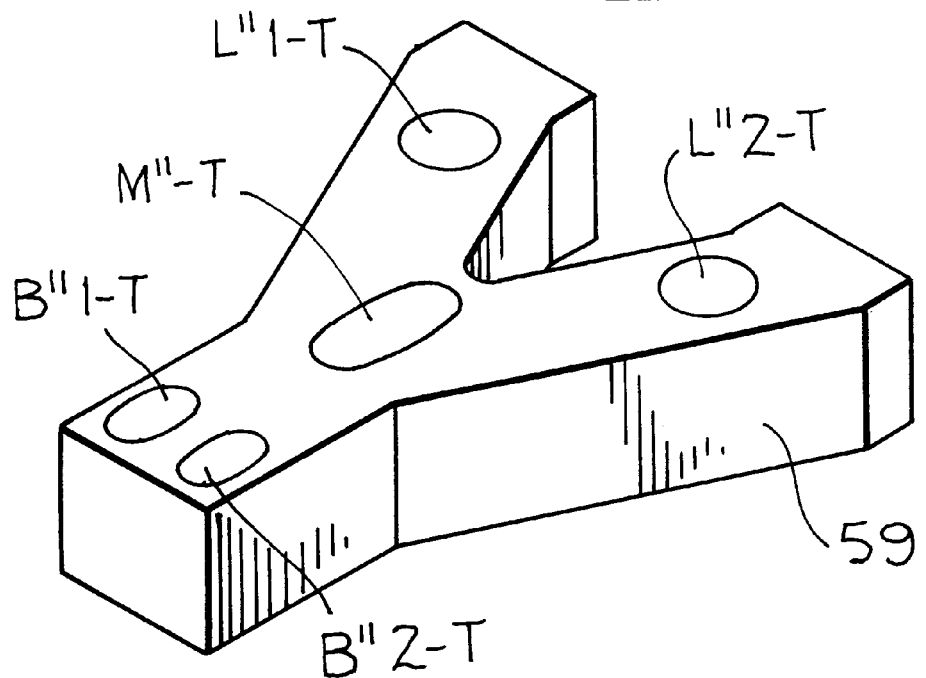
fig_7

PIEZOELECTRIC GLIDE HEAD

BACKGROUND OF THE INVENTION

1. Field of the Invention

The present invention pertains to glide heads for determining the uniformity of the flat surfaces of rotating recording disks by sensing bumps or asperities thereon, and more particularly, it pertains to glide heads of a type which can not only determine the presence of asperities of greater than a predetermined maximum height so as to be useful in determining the necessity of further burnishing operations but also accurately map or locate the asperities on the recording disk face so as to provide disk quality control information for possible adjustment of the disk manufacturing process parameters.

2. Description of the Prior Art

The basic memory storage device of computers today is the rigid magnetic disk, or so called hard disk, which includes a thin magnetic film on both of its surfaces to which information can be written or read by tiny magnetic transducer heads suspended from actuator arms which are adapted to be moved radially across the surfaces of the disk. The magnetic information is commonly imparted to the disk in a series of concentric tracks extending radially about the disk surfaces. As the disk is rotated, information is transferred between each magnetic head and the disk with the head being spaced from the disk surface by only a very small air bearing distance so that the magnetic head does not ride directly upon and damage, or be damaged by, the disk surface. With the ever increasing demand for higher disk storage capacities, the number of magnetic tracks on the disk is increasing while the spacing thereof is decreasing, and the number of individual magnetic bits per unit distance along each track is increasing; consequently, the magnetic head must ride ever closer to the surface of the disk in order to properly write information on and read magnetic information from the disk. In today's market the flying height of such data heads over the disk has been reduced to about 1–2 microinches, and this distance is shrinking and will continue to shrink as the bit storage capacity for unit area on the disks increases. Obviously, in order to avoid collisions between the magnetic head and the disk during the reading/writing operation of the head, the disk surface relative to the flying height of the magnetic head must be flat, stable, and free from protrusions, or asperities, rising above the flat surface of the disk which asperities could cause damage to the magnetic heads and which could cause errors in writing to or reading from the magnetizable plane in the disk adjacent to the disk surface.

Magnetic disks are typically comprised of a substrate of aluminum/magnesium alloy upon which a thin layer of magnetic film is sputtered with the magnetic film being adapted to be magnetized and read by the magnetic head passed thereover. The disk is then typically overcoated with a thin layer of carbon at a thickness at about 5–250 angstroms to provide protection for the disk surface. This protective layer provides erosion resistance and damage protection from impact and is adapted to be sputtered onto the disk. It will be appreciated, however, that none of the manufacturing processes can be absolutely perfect and that asperities can develop on the disk surface, i.e., rough areas where the surface elevation will vary. Such asperities may be large enough to permit the disk to contact the magnetic head as it travels over the rapidly moving disk surface, and consequent damage to the disk can occur as mentioned above. Even if head/disk collisions do not occur, shock waves created in the magnetic head due to the change in air pressure therebetween caused by an asperity on the disk surface can result in the miswriting or misreading of magnetically encoded information on the disk surface. In view of the foregoing, it is a standard process in magnetic disk manufacture to pass a glide head over the disk surface, in a manner somewhat similar to the manner in which the magnetic heads will be passed over the surface during subsequent read/write operations, in order to test the surface for asperities in order that such asperities may be eliminated or reduced in size by subsequent burnishing operations. Furthermore, it has become conventional to use such glide heads to locate and map the location of the asperities on the disk surface in order to provide corrections in the manufacturing process, if necessary, in order to achieve a more perfectly flat and planar surface on the disk.

The glide heads are generally comprised of a slider, much like the sliders used in the conventional read/write magnetic heads, which slider is flexibly supported from a flexure arm and which includes a pair of radially spaced flight rails, or other configurations of air-bearing surfaces, that cause the slider to ride above the disk with a slight backward tilt whereby the trailing edge of the slider rides on an air bearing surface at a very close spacing to the disk surface. This slide head-to-disk surface spacing will typically be somewhat less than the spacing of the read/write magnetic head when the finished recording disk is used in data transfer operation. A piezoelectric transducer is located on the glide head, and electrical leads are provided from the transducer to appropriate external circuitry so that stresses in the piezoelectric element created by collisions or near misses between the glide head and the disk surface (i.e., rapid changes in sensed pressure) due to asperities on the surface of the disk can be monitored.

Depending on how the piezoelectric transducer is positioned on the slider, it has been conventional to look for an electrical output signal with a dominant frequency band, i.e., a natural frequency of vibration of the slider/piezoelectric transducer in a particular mode or plane due to glide head/disk surface interference. That is to say, as the glide head flies over the disk, any asperities or protrusions above the nominal disk surface elevation sufficient to cause a change in pressure at the trailing edge of the slider will induce a dominant mode of vibration in the piezoelectric transducer which can be read and interpreted in a manner so as to define the nature of the asperity. Because the sensing edge of the slider will extend for some distance radially of the rotating disk, and since the sensing edge of a slider will not be uniform due, typically, to the presence of the requisite spaced flight rails defining the same, it will be apparent that asperity/glide head interference will produce a number of different vibrational modes in the piezoelectric transducer which will occur in locations and at frequencies as determined by the size and shape of the piezoelectric element and (particularly) its location with respect to the contact point on the slider element as well as by the location and magnitude of the asperities creating the vibrations in the glide head. For example, an asperity which contacts only one flight rail of the slider element will produce a distinctly different set of vibrational modes in the transducer than a pair of asperities of a similar elevation which contact both flight rails at the same time.

The foregoing factors have created difficulties in obtaining reliable readings from the glide heads so that the exact nature and height of asperities can be determined in order to know whether the requisite "flatness" of the disk has been obtained or whether further burnishing operations are required. Even greater problems are encountered with conventional glide heads in determining the specific location and extent of asperities on the disk surface due to the various modes of vibration which are set up in the transducer element which in some cases may cancel each other out or be unrealistically combined.

One method of obtaining a more reliable and informative reading from a glide head is shown in prior U.S. Pat. No. 5,423,207 to Flechsig et al.; U.S. Pat. No. 5,450,747 to Flechsig et al.; U.S. Pat. No. 4,532,802 to Yeak-Scranton et al., and IBM Technical Disclosure Bulletin Volume 34, No. 4a, September 1991, page 459. These prior art disclosures generally show glide heads which include, not one, but a plurality of separate transducers affixed to the body of the slider element which transducers can be separately monitored with the outputs thereof being compared so as to provide a better analysis of the surface of the disk being monitored.

Another method of more reliably obtaining a transducer output or reading which accurately reflects the surface contours of the recording disk being monitored is shown in U.S. Pat. No. 5,689,064 to Kennedy et al. Here, the transducer element does not directly overlie the slider element (as is conventional in most prior art devices) but is attached to the slider only at one narrow face thereof so as to extend laterally of the slider in cantilevered fashion whereby the dominant mode or modes of vibration of the transducer element can be more accurately determined and appropriate filtering circuitry can be utilized to obtain more reliable glide head readings.

SUMMARY OF THE INVENTION

With the present invention, a piezoelectric glide head and method of glide head testing flat rotating recording disk surfaces are provided which permit more accurate information to be gathered with regard to both the size and specific location of asperities or other anomalies on the recording disk surface.

Since various modes of vibration may be excited in the glide head slider element by the passing of a single surface anomaly beneath a particular part, i.e., the sensing edge or edges, of the slider flight surface, it is important that the particular modes of vibration of interest be isolated by first designing the piezoelectric element itself with a particular geometry so as to accentuate such particular modes of vibration, and then particularly sensing the stresses at specific locations on the piezoelectric element where they are maximized so as to obtain a good signal-to-noise ratio and eliminate or minimize the effects of the other, non-relevant modes of vibration. Thus, the piezoelectric transducer of the present invention is designed with such geometry and is attached to the anomaly sensing slider element only at one small face thereof so that the various modes of vibration induced in the slider element will be transferred to the piezoelectric element as shock waves having particular vectors.

The glide head of the present invention may thus utilize a more or less conventional slider element having a typical air bearing surface on a face thereof that includes a sensing edge or edges (usually at the trailing edge of the air bearing surface) which glide over the flat disk surface to obtain the relevant surface contour or anomaly location information. The particular construction of the slider, or sensor element, is immaterial except insofar as it affects the particular algorithms to be used in determining the magnitudes and locations of the disk surface anomalies. The piezoelectric transducer element is attached to the slider in a cantilevered fashion and is shaped in a segmented manner so as to accentuate the shockwaves propagated from the slider in at least two different linear directions. A plurality of spaced electrodes are then positioned on at least one of the opposed surfaces of the piezoelectric element so that a plurality of stress level readings can be obtained for the stresses caused by different modes of vibration occurring in the piezoelectric element in the two linear directions, which preferably would include a "bending mode" in the direction of relative motion of the disk and slider and a "twisting mode" at a transverse direction thereto. Appropriate processing or analyzing circuitry may then be connected to the electrodes so that the various independent readings from the transducer element can be compared, e.g., in amplitude, time, and phase, to more accurately define the nature of any asperities or anomalies encountered and their location on the recording disk being tested.

In the preferred arrangement the piezoelectric transducer element is attached to the trailing end of the slider so as to extend in the direction of relative motion of the slider and rotating disk surface. The transducer is shaped in a laterally extending, legged fashion (e.g., as a V, Y, or T) so that readings may be obtained in one or more modes of vibration extending in the direction of disk/glide head relative motion (bending mode) and one or more modes of vibration in the twisting mode transversely to the direction of relative motion.

BRIEF DESCRIPTION OF THE DRAWINGS

FIG. 1 is a diagrammatic elevation view of a glide head system which includes two glide head assemblies for testing for surface asperities on both sides of a rotating recording disk.

FIG. 2 is an enlarged perspective view of the upper one of the glide head assemblies diagrammatically illustrated in FIG. 1.

FIG. 3 is an enlarged exploded view of the distal end of the glide head assembly of FIG. 2 illustrating in greater detail the component parts thereof prior to assembly.

FIG. 4 is an enlarged bottom plan view of a portion of the glide head of FIG. 2 showing the piezoelectric transducer element and the electrical connections thereto along with a portion of the slider element.

FIGS. 5A, 5B, 5C, 5D, and 5E are circuit diagrams illustrating typical circuits to which the various electrodes of the transducer element of the glide head of FIG. 4 can be connected in order to obtain pertinent output information with respect to the surface anomalies of the recording disk surface.

FIG. 6 is an isometric view of an alternative transducer element configuration particularly illustrating the location of the sensing electrodes at the various areas of maximum stress concentrations as the slider element of a glide head encounters various types of asperities or anomalies on the tested disk surface and generates various modes of vibration in the transducer element.

FIG. 7 is an isometric view of a further embodiment of the transducer element of the glide head of the present invention particularly illustrating the locations of the sensing electrodes at the areas of maximum stress concentrations when various types of asperities or anomalies are encountered by the slider element of the glide head and generate various modes of vibration in the transducer element.

DESCRIPTION OF THE PREFERRED EMBODIMENTS

Figure 8A:
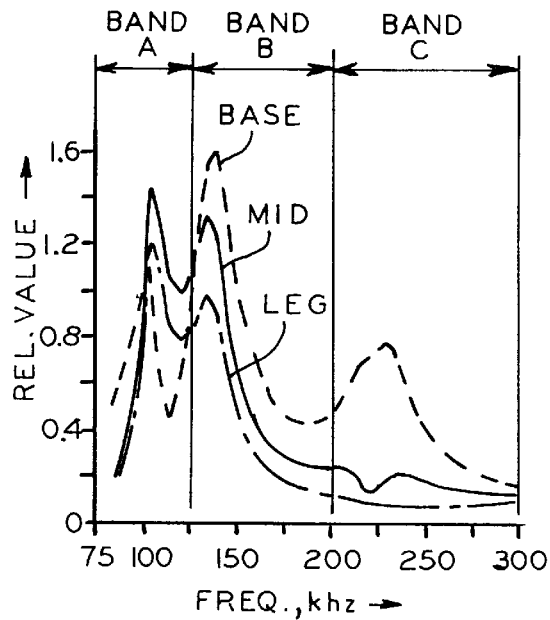
FIGS. 8A and 8B are graphs illustrating the relative output signal magnitude of the piezoelectric transducer at different locations thereon over the frequency spectrum of 75–800 khz where an asperity engages one rail only of the sensing edges of the slider.

FIG. 1 shows diagrammatically the novel glide head 22 of the present invention in a more or less conventional glide head arrangement for testing for asperities or anomalies on the opposed surfaces of a flat magnetic recording disk 10. The recording disk is appropriately fixed upon an upright spindle 11 and is adapted to be rotated by the spindle (by means not shown) about a vertical axis 12 where its upper surface can be tested by a glide head assembly 14 and its lower surface can be tested by a glide head assembly 16. Each of the glide head assemblies 14 and 16 is secured to a driver mechanism 18, 20, respectively, so that they may be moved in the radial direction of the disk 10, and each of the glide head assemblies 14, 16 includes the glide head 22 at its distal, or projecting, end which includes a sensing edge adapted to ride on an air bearing at a very close spacing to the disk 10 surface when the disk 10 is rotated at a sufficient rotational speed. The glide head assemblies further include means to send a plurality of electrical signals therefrom to a signal processor 24, such signals being indicative of shock waves created by a sudden change in pressure sensed by the glide head which, in turn, is indicative of the presence of an asperity or anomaly on the surface of the recording disk 10.

Since the glide head assemblies 14 and 16 are identical except that the assembly 14 is spring loaded so as to ride adjacent the upper surface of disk 10 while assembly 16 is spring loaded so as to ride adjacent the lower surface of disk 10, only glide head assembly 14 will be described in detail hereinafter to illustrate the principles of the present invention. It will be understood that glide head assembly 16 is similarly constructed and operates in the same manner.

Glide head assembly 14 is shown in expanded detail in FIG. 2 of the Drawings and will be seen to essentially be comprised of an elongated, tapered flexure 26 which is provided with a mounting pad 27 at one end thereof which pad has a pair of laterally spaced mounting holes 28, 29 permitting the flexure to be bolted or otherwise rigidly attached to the driver mechanism 18. Flexure 26 is formed of a thin metallic material so that it may provide a spring or flexing pressure to maintain the glide head in close, gas lubricated (air bearing) proximity with the surface of the disk 10 to be tested. As can be seen from FIG. 2, the flexure tapers from the mounting pad 27 outwardly to the unsupported distal end which terminates in a tongue 30 that is secured to the lowermost surface of the flexure in a manner to be explained in greater detail hereinafter. The underside of tongue 30 is designed to support the glide head 22 which will be seen to be a composite structure including a slider 36 and a piezoelectric transducer 38 which is rigidly attached to one face of the slider so as to extend therefrom in cantilevered fashion. Twisted wire pairs 40 are attached to various electrodes 42 on the opposed (top and bottom) surfaces of the transducer to provide electrical output signals indicative of the stress therebetween. As can be seen in FIG. 2, the twisted wire pairs 40 are directed to a tubular conduit 44 which extends along the longitudinal axis of the flexure 26 and off of the supported, or driven, end of the flexure adjacent pad 27 to a position where it can be conveniently directed to the signal processor 24 located externally of the moving apparatus, as in conventional glide head arrangements. In place of the twisted wire pairs 40, conventional flex circuitry may be used to establish the electrical connection between the electrodes 42 and the signal processor 24.

A portion of the flat recording disk 10 being glide head tested is shown in FIG. 2. As is conventional, information may subsequently be magnetically recorded on the surface S of the disk 10 in closely spaced concentric tracks by means of a magnetic recording head attached to the undersurface of a slider that is very similar in construction to the slider 36 of the glide head. Thus, as previously explained, it is essential that the surface S be as flat as possible so that when the magnetic recording head flies over the disk at heights which may be as little as 1–2 microinches, no asperities, i.e., protrusions, are present which will collide with the recording head or narrowly miss it so as to induce a shock wave therein potentially causing damage to the head or disk surface as well as leading to incorrect reading/writing of magnetic information to or from the disk.

While it has been traditional to look for asperities on the surface of the disk, i.e., protrusions above some nominal surface level of the disk, it will be understood that depressions or pits, if of sufficient depth and definition, can similarly cause read/write errors between the magnetic recording head and the disk and therefore the more general terminology "anomalies" will be given to those surface level imperfections which the glide head of the present invention is designed to detect. It will be understood that with the glide head 22 of the present invention, it is the shock waves induced in the slider 36 which are, in turn, transmitted to the piezoelectric transducer 38 through the relatively small surface area of the transducer/slider interface which are isolated in and measured by the transducer. Since the slider 36 has a sensing edge on its undersurface closely spaced from the disk and since a high rate of change of pressure per unit time (dp/dt) at such sensing edge will induce a shock wave into the slider 36, various anomalies on disk surface S can create shock waves in the transducer 38 even if the slider is not struck by a protrusion on the surface S of the disk.

In the glide head arrangement shown in FIGS. 1 and 2, the driver mechanism 18 is designed to move the glide head assembly in the direction of the arrow A (FIG. 2) so that the sensing edge on the undersurface of the slider 36 will move along a path generally radially of the disk 10 as indicated by the line R in FIG. 2. Obviously, other types of drivers may be used, e.g., pivotable drivers similar to those used in conventional magnetic disk drives with the sensing edge moving along an arcuate path generally radially of the disk 10 (varying but slightly therefrom as the skew angle of the slider changes from the outer to the inner radius of the disk. The slider 36, as shown in FIG. 3, is formed in a conventional slider geometric shape known in the industry as the "50%" slider, although any other conventional slider or sensor member having a generally radially extending sensing edge or edges could be utilized equally as well in accordance with the principles of the present invention. With the disk spinning in the direction as indicated by the arrow in FIG. 2, the sensing edge will be located at the trailing edge 37 of the slider where the slider is closest to the disk as the disk is rotated. In order to further insure this and to prevent unexpected contact between the slider and the disk surface S, the leading edge of the slider is chamfered at 39 so that the slider is tilted slightly upwardly from trailing edge 37 to the chamfered edge 39 under the force of the air flowing therebeneath. In practice, with a conventional 50% slider of approximately 80 mils in length, the tilt of the slider will be very slight, i.e., in the range of about 15 microinches from front to back, i.e., along the 80 mil longitudinal dimension of the slider.

The glide head 22 structure at the projecting end of the flexure 26 is shown in greater detail in the exploded view of FIG. 3 and in the bottom plan view of FIG. 4. It will be seen that the tongue 30 at one end thereof is provided with a tooling hole 48 which can be matched with a similar tooling hole 49 in the body of the distal end of flexure 26 so that the tongue can be correctly positioned at the end of the flexure 26, the tongue and flexure being thereafter rigidly secured together by means of laser welding or the like. It will also be noted, from FIG. 3, that the tongue 30 is provided with a flexible cutout section 46 extending rearwardly from the projecting end of the tongue and including a raised knob 50 on the upper portion thereof. The slider 36 is rigidly attached by an adhesive 47 to the underside of the flexible extension 46, as indicated. The piezoelectric transducer 38 is securely and rigidly fastened onto the front face 36a of the slider, as indicated in FIG. 3, by means of a suitable adhesive 51 so as to project from the trailing edge of the slider. When the assemblage of FIG. 3 is secured together as indicated and the flexure 26 is moved into position above the rotating disk 10, the raised knob 50 atop the extension 46 of tongue 30 abuts against the underside of the flexure 26 so as to provide a universal pivotal support for the slider 36 allowing it to adjust to the various flight attitudes necessitated by variations in the mounting of the disk 10 and its dimensions, surface runout, etc.

It will be recognized that the geometry of the slider 36 is conventional including a longitudinally extending channel 52 on the flight surface thereof formed by a pair of rails 54 and 56 along the outer and inner radial edges of the slider, respectively, to provide the slider with the appropriate flight characteristics as the disk surface S is rotated therebeneath at the appropriate speed. This speed may be somewhat less than the disk speed under read/write operations since, as previously pointed out, the glide head should fly at a closer spacing (about one-half to three-quarters) of the normal spacing used during data transfer. It will also be recognized that the sensing edge at the trailing end of the slider 36 is comprised of a pair of laterally spaced edges 37a and 37b.

With this conventional slider construction, it has herebefore proven to be difficult to correctly measure the height of asperities or determine other anomalies on the face of the disk, and more particularly, to pin-point the exact location of such anomalies on the disk so that the manufacturing parameters might be altered if necessary to provide a truly flat finished disk. It will be recognized, for example, that an asperity might contact one sensing edge (e.g., 37a) of the slider while another asperity, or no asperity at all, might contact or be vertically aligned with the other sensing edge 37b. Such different circumstances will generate different vibrational modes in the piezoelectric transducer element of conventional glide heads which may cancel each other at any particular frequency or which may otherwise combine to provide ambiguous output signal information.

In order to overcome the foregoing problem, the piezoelectric element 38 of the present invention is attached to the slider only on the trailing face thereof so that all vibrations from the slider are delivered to the transducer element through a single connecting plane forming a relatively small surface area on the transducer. Transducer 38 thus extends in cantilevered fashion from the slider, and it is formed in a segmented, or legged, shape so that the different vibrational modes transmitted from the slider (due to anomaly interference) will be accentuated in at least two different linear directions. In the preferred embodiment of the invention, as shown in FIGS. 3 and 4, the transducer 38 is formed in a V-shape with the major axis L (FIG. 3) of the V extending in the direction of relative motion between the slider and the disk surface S at the line of sensing contact (i.e., sensing edges 37a, 37b), and the legs 38a and 38b of the transducer (FIG. 3) extend laterally of such axis so as to accentuate the twisting mode of vibration in the radial direction R (FIG. 2), such as might be generated when an asperity strikes one of the rails 54, 56 but not the other.

In contrast with the prior art devices wherein the electrodes or conductive elements of the transducer are provided either over the entire surface of the piezoelectric transducer or at specific geographic locations on the slider, the electrodes 42 of the present invention are located specifically at those points in the segmented transducer which have been determined to isolate specific modes of vibration set up in the slider 36. While only one of the top and bottom surfaces of transducer 38 need be provided with separate, spaced electrodes, in the preferred arrangement (as shown) spaced pairs of electrodes are provided about both of the opposed major surfaces of the transducer to better isolate the electrical signals from the critical stress locations therein. Thus, the electrodes 42 have been arranged in pairs between the top surface T (FIG. 3) and the bottom surface B (FIG. 4) which pairs have been positioned in specific geographic locations on the transducer; namely, at the radial inner edge of the base adjacent the slider (B1), at the radial outer edge of the base adjacent the slider (B2), at a midpoint just below the separation of the legs (M), and approximately midway out each of the legs 38a and 38b (L1 and L2). Thus, five sets of vertically aligned electrodes are provided as seen in FIGS. 3 and 4 and designated as sets B1-T and B1-B, B2-T and B2-B, M-T and M-B, L1-T and L1-B, and L2-T and L2-B. The top and bottom electrodes of each pair are connected to one of the twisted pairs of conductors 40 and thus provide the input signals to the signal processor 24 where they can be measured and compared as will be explained in greater detail hereinafter. As can be seen from FIG. 3, the twisting wire pairs 40 are retained by conduit 44 which is arranged to be secured in position at the distal end of flexure 26 by a bracket 53.

It will thus be understood that shockwaves created in the slider 36 by anomalies on the surface S of recording disk 10 will be transferred to the piezoelectric transducer 38 through its rather small area of contact on the narrow face 36a of the slider. These shockwaves will be transformed into different modal frequencies at different magnitudes in the piezoelectric transducer depending upon the magnitudes of the shock wave in the slider and their arrival vectors into the transducer at the plane of attachment on face 36a. Of particular interest in the present invention are the "bending" vibrational mode aligned in the relative direction of motion (the arrow L in FIG. 3), which primarily determines the magnitude of the anomaly, and the "twisting" mode of vibration extending at right angles thereto generally in the direction of the arrow R of FIG. 2 which primarily determines the radial location of the anomaly. It will be understood that further conventional circuitry (not shown herein) will track and establish the circumferential location on the disk of the anomaly which is readily accomplished since the modal frequencies of vibration being analyzed will be damped out after an insignificantly small amount of travel of the glide head over the disk surface.

Since the modal frequencies of vibration will vary considerably as the dimensions of the slider 36 or transducer 38 or the method and location of connection therebetween are varied, it is important that each glide head structure (slider/transducer) be first tested with a frequency spectrum analyzer to determine where the peak signals are obtained under various types of disturbances to the slider 36. This information can then be used to compare the signals from the various sets of electrodes in frequency, amplitude, and phase relationships in order to properly identify both the size of the anomaly on the surface S and the location thereof.

By way of example, with the present invention utilizing a conventional 50% slider of the catamaran type (two-rail) which is 80 mils in length (in the direction of arrow L of FIG. 3), 63 mils wide (dimension Y4 in FIG. 4), having rails 54, 56 about 10 mils wide (the length of sensing edges 37a, 37b), and including a recessed flight surface 52 of about 5 mils in depth (i.e., the rails 54, 56 are 5 mils deep). With such a slider geometry, the piezoelectric transducer 38 was chosen having a V-shape with dimensions, as indicated in FIG. 4, as follows: Y1=124 mils; Y2=46 mils; Y3=39 mils; and Y5=30 mils. The thickness of transducer 38 is about 25 mils; thus, the transducer is attached to the face 36a of the slider only over a 25×30 mil rectangular surface area.

Figure 8B:
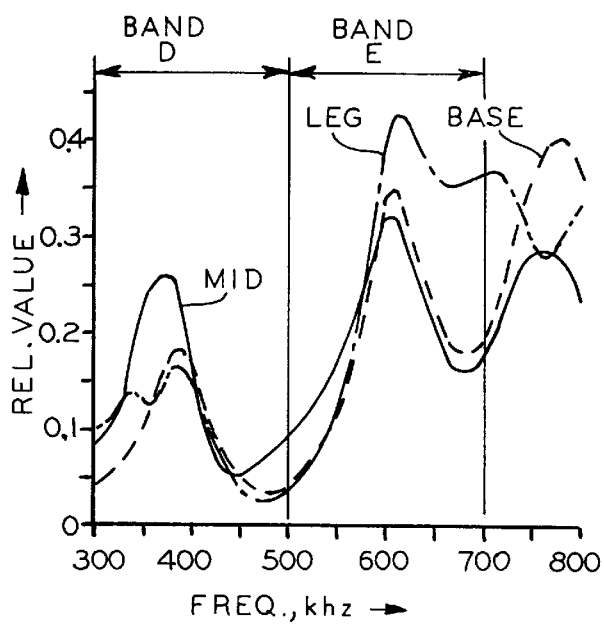
Figure 9A:
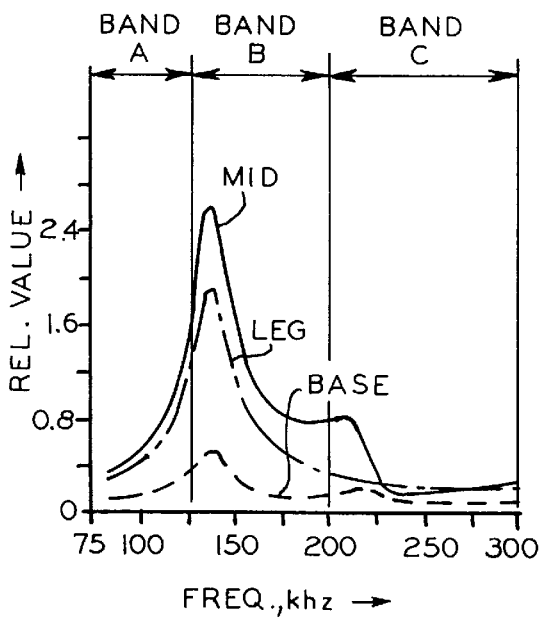
FIGS. 9A and 9B are graphs illustrating the relative output signal magnitude of the piezoelectric transducer at different locations thereon over the frequency spectrum of 75–800 khz where an asperity or asperities engages both rails of the sensing edges of the slider.
Figure 9B:
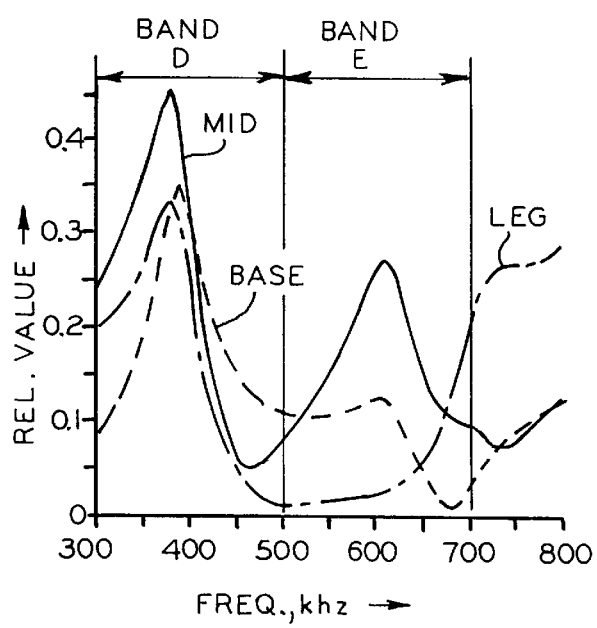

With a glide head 22 of the dimensions aforedescribed, a computer dynamic structural stress analysis was conducted under two model stimulation conditions using ANSYS software. One program was run with stimulation of the model (glide head 22 as aforedescribed) at one sensing edge 37a,37b only, and the second program was run with stimulation of the model equally at both sensing edges. FIGS. 8A and 8B illustrate the frequency spectrum from the computer analysis over a frequency range from 75 kilohertz–800 kilohertz at the transducer locations of the electrodes B1 (base), M (mid), and L1 (leg) using the first model stimulation program (i.e., only one edge stimulated). A subsequent empirical analysis using an actual glide head 22 as aforedescribed and electrical measurements from the electrodes 42 as shown confirmed the results of the computer analysis. FIGS. 9A and 9B similarly show the frequency spectrum (75–800 khz) from the computer analysis for the second program wherein the model stimulation approximates that which occurs when both of the slider sensing edges 37a,37b are simultaneously contacted by asperities, such Figures indicating the frequency spectrum for the model locations corresponding to the base, mid and leg electrode locations. From the results of the computer analysis with the particular configuration and dimensions of glide head 22 as aforedescribed, it has proven to be convenient to break up the frequency spectrum into five bands as indicated in FIGS. 8A, 8B, 9A, and 9B including a band A extending from 75 kilohertz to 125 kilohertz, a band B extending from 125 kilohertz to 200 kilohertz, a band C extending from 200 kilohertz to 300 kilohertz, a band D extending from 300 kilohertz to 500 kilohertz, and a band E extending from 500 kilohertz to 700 kilohertz. By providing multiple band pass filters, such as a comb filter or the like, to limit the output of the various electrode pairs 42 to these particular narrow frequency bands, comparisons and measurements can be made to determine both the location and size of the anomalies on the disk surface S. Algorithms can be readily developed and rather elementary processing circuitry, forming a portion of the signal processor 24, can be utilized as particularly shown in FIGS. 5A–5D to make the appropriate determinations.

From a consideration of the frequency spectrum analysis of FIGS. 8A and 9A, it would appear that the output of the midtop (M-T) and midbottom (M-B) electrode pair in band B is a good reference point for an accurate indication of the degree of disturbance generated in the slider due to the anomaly on the disk surface. The M-T/M-B electrode pair may also be used as the reference to determine the phase relationships to the other electrode pairs in order to determine the radial location (i.e., inner or outer rail disturbance) of the anomaly. Thus, as shown in FIG. 5A, the signal output from M-T and M-B may be applied to a differential amplifier 60 having appropriate impedance input characteristics and a band pass filter 62 tuned to band B (125–200 kilohertz) and passed to a peak detector 63 to provide an output signal indicative of the stimulation magnitude of the anomaly since, as can be seen from FIGS. 8A and 9A, a peak signal will occur at about 135 kilohertz irrespective of whether one or both of the rails are stimulated. By applying the same signal from M-T, M-B to the similar circuitry of FIG. 5B including amplifier 65, band pass filter 66, and peak detector 67 with the band pass filter being limited to band A (75–125 khz) as shown in FIG. 5B, only the stimulation of one of the rails will create a significant signal output, and the signal from the 5B circuitry will indicate the degree of asymmetry between the stimulation of the two rails or sensing edges 37a,37b. Thus, by comparing the stimulation magnitude output of FIG. 5A and the degree of asymmetry signal from FIG. 5B one can obtain an indication of both the magnitude of the anomaly or anomalies and whether or not one or both rails are being stimulated. To further determine whether the inner or the outer rail is stimulated, i.e., the direction of asymmetry, the circuit of FIG. 5C may be used. In this circuit arrangement, the base electrode pairs B1 and B2 are utilized, with the circuitry as shown in FIG. 5C, and with the signals therefrom being separately passed through amplifiers 70,71 to band pass filters 72,73, each tuned to band B, and to peak detectors 74,75 and with the outputs thereof being directed through a differential amplifier 76 to determine the magnitude of the difference between the input signals and indicate the direction of the asymmetry, i.e., which of the sensing edges 37a,37b is being stimulated. From a comparison of FIGS. 8A and 9A, it will be apparent that the base electrodes B1,B2 will give a strong signal when one only of the sensing edges 37a, 37b is stimulated, whereas a very small signal is produced in this frequency range if both sensing edges 37a, 37b are similarly stimulated.

By utilizing bands D and E (as shown in FIGS. 8B and 9B) and the leg electrode pairs L1 and L2, a further determination of the stimulation magnitude and degree of asymmetry (difference in stimulation between the inner and outer sensing edges 37a, 37b) can be obtained. Thus, as shown by the circuitry of FIG. 5D which forms a portion of the signal processor 24, the output of one of the electrode pairs L1-T,L1-B can be passed through a differential amplifier 80, a band pass filter 81 (tuned to band D), and a peak detector 82 to provide an output signal indicative of stimulation magnitude since, as seen in FIGS. 8B and 9B, the signals within this narrow frequency band will be relatively unaffected by asymmetry in the manner of excitation of the sensing edges 37a,37b. However, a comparison of FIGS. 8B and 9B clearly indicates that a strong peak signal in the leg electrodes occurs at about 625 kilohertz when only one leg is stimulated whereas no such peak occurs if both legs are similarly stimulated. Thus, by applying the signal from the second leg electrode pair L2-T, L2-B to a circuit comprised of differential amplifier 84, band pass filter 85 tuned to band E, and a peak detector 86, the output signal, as shown in FIG. 5E, will provide an indication of the degree of asymmetry between the stimulation to the inner and outer sensing edges 37a, 37b.

While specific circuit details have not been provided herein, it will be recognized that other specific circuit arrangements are possible and other algorithms can be used in determining the specific location and nature of the anomalies detected by the sensing edges of the glide head 22 of the present invention. Thus, by utilizing specific phase detection circuitry on the various electrode pairs and using the midtop (M-T, M-B) pair as a reference point, the phase of the two electrode sensors on the legs and the two electrodes sensors at the base can be compared to clearly indicate the radial direction of the disturbance relative to the centerline of the slider 36. It will also be understood that the specific frequency ranges selected and algorithms developed are for the specific glide head configuration chosen, any change in materials, dimensions, or geometric design will change these factors also.

It is also important to note that since the electrodes are limited to small geographic areas on the transducer which have been chosen to maximize stresses in particular vectored directions of vibration as transferred from the slider, the tendency for different modal frequencies in the transducer to cancel each other or otherwise provide erroneous readings will be largely eliminated.

It should also be noted that algorithms can be developed without using only the electrode pairs L1-T and L1-B, L2-T and L2-B, M-T and M-B, etc. Signals may be derived from separate combinations of electrodes on the same transducer surface, i.e., L1-T and M-T, as well as on the opposed surfaces.

While the foregoing description of the piezoelectric transducer element has been limited to a V-shaped configuration, it is evident that other segmented shapes may be similarly utilized in accordance with the present invention. For example, FIG. 6 illustrates a T-shaped transducer element 58 having five pairs of electrodes spaced about its opposed surfaces as shown, namely, L'1, L'2, M', B'1, and B'2. Similarly, FIG. 7 shows a Y-shaped piezoelectric transducer 59 also having five spaced electrode pairs, namely, L"1, L"2, M", B"1, and B"2. In a manner similar to that described hereinbefore, a frequency spectrum analysis can be made of the output signals from the various electrode pairs of the transducers of FIGS. 6 and 7 so as determine the various band pass filter combinations and other circuit elements to utilize in providing a means for accurately determining stimulation magnitude and location of the anomalies or asperities on the disk surface.

It is also important to note that the operational principles outlined herein do not require that the transducer element be attached in cantilever fashion at the trailing edge of the slider, or sensing element, but it may extend from other faces of the slider which, as previously pointed out, may be of various other designs and with various other types and locations of sensing edges.

Although the best modes contemplated for carrying out the present invention have been hereinshown and described, it will be apparent that other modifications and variations may be made without departing from what is regarded to be the subject matter of the invention.

What is claimed is:

1. A piezoelectric glide head for detecting surface anomalies on a continuously rotating flat disk surface comprising:

a slider having a flight surface on one side thereof with a leading end and a trailing end at opposite ends of said flight surface in the longitudinal direction of the slider, said flight surface including at least one sensing edge extending in a direction transverse to said longitudinal direction, said slider being adapted to be supported so that said flight surface faces said disk surface with the disk surface being arranged to move from the leading end of the slider to the trailing end thereof as it rotates adjacent to the slider, the configuration of said flight surface and the slider support causing the slider to pitch away from the disk surface at the leading end thereof so that the sensing edge rides on an air bearing adjacent to and at a close spacing to said disk surface;

a piezoelectric element secured to the slider and extending outwardly therefrom in cantilevered fashion, said element having a pair of opposed surfaces facing towards and away from said disk surface and having a shape so as to accentuate shock waves from the slider in at least one particular linear direction;

electrodes positioned on said opposed surfaces of the cantilevered piezoelectric element with at least one of such surfaces being provided with a plurality of spaced electrodes positioned about the surface of the piezoelectric element to provide different stress readings for the modes of vibration imparted to the slider by anomalies on said flat disk surface;

and electrical leads connected to said electrodes for direction to circuitry for determining the nature of the anomalies on said disk surface which create said modes of vibration in the slider.

2. A glide head according to claim 1 wherein said shape of the piezoelectric element is segmented so as to accentuate said shock waves in two generally orthoganal directions and wherein the spacing of the electrodes is such as to provide different stress readings in said orthoganal directions.

3. A glide head according to claim 2 wherein one of said two orthoganal directions is in alignment with the relative direction of motion of the slider and disk surface at the sensing edge of the slider and the other of said directions extends generally in the radial direction of said rotating disk surface.

4. A glide head according to claim 3 wherein said piezoelectric element extends along the longitudinal axis of said slider in a direction generally aligned with said relative direction of motion of the slider and disk surface.

5. A glide head according to claim 4 wherein said piezoelectric element includes legs extending laterally of said longitudinal axis.

6. A glide head according to claim 1 wherein both of said opposed surfaces of the piezoelectric element are provided with a plurality of said electrodes, said electrodes being arranged in spaced pairs between said opposed surfaces with the electrode of each pair being aligned transversely to said opposed surfaces.

7. A multimode piezoelectric glide head for mapping the size and location of anomalies on a continuously rotating disk surface comprising:

a slider having a flight surface on one side thereof with a leading end and a trailing end at opposite ends of said flight surface in the longitudinal direction of the slider, said slider including at least one sensing edge extending in a direction transverse to said longitudinal direction, said slider being adapted to be supported so that said flight surface faces said disk surface with the disk surface being arranged to move from the leading end of the slider to the trailing end thereof as it rotates adjacent to the slider, the configuration of said flight surface and the slider support causing the slider to pitch away from the disk surface at the leading end thereof so that the sensing edge rides on an air bearing adjacent to and at a close spacing to said disk surface;

a piezoelectric element secured to the slider and extending outwardly therefrom in cantilevered fashion, said element having a pair of opposed surfaces facing towards and away from said disk surface and having a segmented shape so as to permit maximum deflections due to shock waves from the slider in a direction parallel to the relative direction of motion of the slider and the rotating surface at said trailing of the slider and in a direction transverse thereto;

electrodes positioned on said opposed surfaces of the cantilevered piezoelectric element with at least one of such surfaces being provided with a plurality of spaced electrodes located at spaced positions on the piezoelectric element in both said direction parallel to said relative direction of motion and said direction transverse thereto in order to provide stress readings for the modes of vibration in two transverse directions as imparted to the slider by the anomalies on said flat disk surface;

and electrical leads connected to said electrodes for direction to circuitry for determining the size and location of the anomalies on said disk surface which create said modes of vibration in the slider.

8. A glide head according to claim 7 wherein said transverse direction generally extends in the radial direction of said rotating disk surface and wherein said piezoelectric element extends along a longitudinal axis from said slider in a direction generally aligned with said relative direction of motion of the slider and disk surface.

9. A glide head according to claim 8 wherein said piezoelectric element includes legs extending laterally of said longitudinal axis.

10. A glide head according to claim 7 wherein both of said surfaces of the piezoelectric element are provided with a plurality of said electrodes, said electrodes being arranged in spaced pairs between said opposed surfaces with the electrodes of each pair being aligned transversely to said opposed surfaces.

11. A multimode piezoelectric glide head assembly for detecting surface anomalies on a continuously rotating flat disk surface comprising:

an elongated flexure including means for connection to a driver at one end thereof and having an opposite end thereof arranged to be positioned adjacent said rotating disk surface;

means for flexibly supporting a slider at said opposite end of said flexure;

a slider flexibly connected to said means for supporting and having a flight surface on one side thereof facing said disk surface with a leading end and a trailing end at opposite ends of the flight surface in the longitudinal direction of the slider, said flight surface including at least one sensing edge extending in a direction transverse to said longitudinal direction, said disk surface being arranged to move from the leading end of the slider to the trailing end thereof as it rotates adjacent to the slider, said flight surface and means for supporting causing the slider to pitch away from the disk surface at the leading end thereof so that the sensing edge rides on an air bearing adjacent to and at a close spacing to said disk surface;

a piezoelectric element secured to the slider and extending outwardly therefrom in cantilevered fashion, said element having a pair of opposed surfaces facing towards and away from said disk surface and having a segmented shape so as to accentuate shock waves from the slider in at least two different planar directions;

electrodes positioned on said opposed surfaces of the cantilevered piezoelectric element with at least one of such surfaces being provided with a plurality of spaced electrodes positioned about the surface of the piezoelectric element to provide stress readings for the modes of vibration in said two linear directions imparted to the slider by anomalies on said flat disk surface;

and electrical leads connected to said electrodes for direction to circuitry for determining the nature of the anomalies on said disk surface which create said modes of vibration in the slider.

12. A glide head according to claim 11 wherein said two linear directions are orthoganal and wherein one of said directions is in alignment with the relative direction of motion of the slider and disk surface at the trailing end of the slider and the other of said directions generally extends in the radial direction of said rotating disk surface.

13. A glide head according to claim 12 wherein said piezoelectric element extends along a longitudinal axis from said slider in a direction generally aligned with said relative direction of motion of the slider and disk surface.

14. A glide head according to claim 13 wherein said piezoelectric element includes legs extending laterally of said longitudinal axis.

15. A glide head according to claim 11 wherein both of said surfaces of the piezoelectric element are provided with a plurality of said electrodes, said electrodes being arranged in spaced pairs between said opposed surfaces with the electrodes of each pair being aligned transversely to said opposed surface.

16. A glide head system for detecting surface asperities on a continuously rotating flat disk surface comprising:

an elongated flexure including means for connection to a driver at one end thereof and having an opposite end thereof arranged to be positioned adjacent said rotating disk surface;

means for flexibly supporting a slider at said opposite end of said flexure;

a slider flexibly connected to said means for supporting and having a flight surface on one side thereof facing said disk surface with a leading end and a trailing end at opposite ends of said flight surface in the longitudinal direction of the slider, said flight surface including at least one sensing edge extending in a direction transverse to said longitudinal direction, said disk surface being arranged to move from the leading end of the slider to the trailing end thereof as it rotates adjacent to the slider, said flight surface and means for supporting causing the slider to pitch away from the disk surface at the leading end thereof so that the sensing edge rides on an air bearing adjacent to and at a close spacing to said disk surface;

a piezoelectric element secured to the slider and extending outwardly therefrom in cantilevered fashion, said element having a pair of opposed surfaces facing towards and away from said disk surface and having a segmented shape so as to accentuate shock waves from the slider in at least two different linear directions;

electrodes positioned on said opposed surfaces of the cantilevered piezoelectric element with at least one of such surfaces being provided with a plurality of spaced electrodes positioned about the surface of the piezoelectric element to provide stress readings for the modes of vibration in said two different directions imparted to the slider by anomalies on said flat disk surface;

and means connected to said electrodes for determining the nature of the anomalies on said disk surface which create said modes of vibration in the slider.

17. A glide head according to claim 16 wherein said two different directions are orthoganal and wherein one of said directions is in alignment with the relative direction of motion of the slider and disk surface at the trailing end of the slider and the other of said directions generally extends in the radial direction of said rotating flat disk surface.

18. A glide head according to claim 17 wherein said piezoelectric element extends along a longitudinal axis from said slider in a direction generally aligned with said relative direction of motion of the slider and disk surface.

19. A glide head according to claim 18 wherein said piezoelectric element includes legs extending laterally of said longitudinal axis.

20. A glide head according to claim 16 wherein both of said surfaces of the piezoelectric element are provided with a plurality of said electrodes, said electrodes being arranged in spaced pairs between said opposed surfaces with the electrodes of each pair being aligned transversely to said opposed surfaces.

21. A method of glide head testing a continually rotating flat disk surface for the presence and location of anomalies thereon using a glide head assembly which includes a slider having a flight surface thereon that includes at least one sensing edge extending in a direction transverse to the direction of relative motion of the disk surface and a piezoelectric transducer that is attached to the slider body so as to extend outwardly therefrom in cantilevered fashion with a shape so as to accentuate shock waves from the slider in at least two different linear directions, said method comprising:

rotating the disk surface adjacent the flight surface of the slider so that the sensing edge of the slider rides on an air bearing at a very close spacing to said flat disk surface while moving the slider radially of the disk surface, obtaining stress readings from a plurality of separate locations on said piezoelectric transducer as the flight surface at said sensing edge of the slider is moved over anomalies on the disk surface which create shock waves that move through the body of the slider to the transducer, and analyzing the stress readings so as to determine both the size of and the radial location of the anomalies on the disk surface.

22. A method of glide head testing according to claim 21 wherein said analyzing step includes a comparison of the stress readings from a single location on said piezoelectric transducer at different frequency ranges.

23. A method of glide head testing according to claim 21 wherein said analyzing step includes a comparison of the stress readings from two different locations on said piezoelectric transducer which are aligned in a direction generally parallel to the sensing edge of the slider.

24. A method of glide head testing a continually rotating flat disk surface for the presence and location of anomalies thereon using a glide head assembly which includes at least one sensing edge extending in a direction transverse to the direction of relative motion of the disk surface and a piezoelectric transducer that is attached to the sensing edge so as to receive shock waves therefrom and which is shaped so as to accentuate said shock waves in at least one linear direction, said method comprising:

rotating the disk surface adjacent to the sensing edge of the glide head so that the sensing edge rides on an air bearing at a very close spacing to said flat disk surface while it is moved generally radially of the disk surface, obtaining stress readings from a plurality of separate and spaced locations on said piezoelectric transducer as said sensing edge passes adjacent to said anomalies on the disk surface which create shock waves that move from the sensing edge to the transducer, and analyzing the stress readings from said spaced locations so as to determine both the size of and the radial location of the anomalies on the disk surface.

25. In a glide head assembly for detecting surface anomalies on a continuously rotating flat disk surface, said assembly including:

a sensor body having a sensing edge arranged to ride on an air bearing adjacent to and at a close spacing to said disk surface, a piezoelectric transducer element secured to the glide head assembly so as to receive shock waves introduced therein at the sensing edge from said disk surface anomalies and extending from the glide head assembly in cantilevered fashion with a pair of opposed surfaces facing towards and away from said disk surface, a plurality of spaced electrodes on at least one of said opposed surfaces of the transducer element so as to provide different stress output signals when said transducer element is stimulated by the sensing of an anomaly on the disk surface by said sensing edge, and a plurality of electrical leads connected to said electrodes for direction to circuitry for comparing the different output signals and determining the nature of said anomaly on the disk surface.

26. In a glide head assembly according to claim 25 wherein said plurality of spaced electrodes are provided on both sides of said opposed surfaces and are arranged in aligned pairs at specific spaced locations on said transducer element.

* * * * *